United States Patent
Tao et al.

(10) Patent No.: US 11,150,220 B2
(45) Date of Patent: Oct. 19, 2021

(54) ONLINE ANALYZERS FOR FLARE GAS PROCESSING

(71) Applicant: Baker Hughes Oilfield Operations LLC, Houston, TX (US)

(72) Inventors: Chong Tao, Winchester, MA (US); Dan Johnson, Houston, TX (US); Aniruddha S. Weling, Wayland, MA (US); Tony Kowal, Houston, TX (US); Yufeng Huang, Andover, MA (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 152 days.

(21) Appl. No.: 16/692,492

(22) Filed: Nov. 22, 2019

(65) Prior Publication Data

US 2021/0156824 A1 May 27, 2021

(51) Int. Cl.
*G01N 33/00* (2006.01)
*G01N 29/22* (2006.01)
*G01N 29/14* (2006.01)
*G01N 29/032* (2006.01)

(52) U.S. Cl.
CPC ........... *G01N 29/032* (2013.01); *G01N 29/14* (2013.01); *G01N 29/221* (2013.01); *G01N 33/0073* (2013.01)

(58) Field of Classification Search
CPC ...... G01N 29/032; G01N 29/14; G01N 29/22; G01N 33/00
USPC .......................................................... 73/587
See application file for complete search history.

(56) References Cited

U.S. PATENT DOCUMENTS

| | | | | |
|---|---|---|---|---|
| 5,816,705 A * | 10/1998 | Vander Heyden | ..... | G01N 25/22 374/37 |
| 5,892,634 A * | 4/1999 | Ito | .......... | G11B 5/553 360/77.08 |
| 7,013,905 B2 * | 3/2006 | Jones | ................... | G05D 11/138 137/12 |
| 10,746,400 B2 * | 8/2020 | Johnson | ............... | G05B 19/418 |
| 2018/0292338 A1 * | 10/2018 | Liu | ..................... | G01N 33/0073 |
| 2020/0225120 A1 * | 7/2020 | Engstrom | ............. | G01M 17/06 |

OTHER PUBLICATIONS

Characterization and Sensing of Inert Gases with a High-Resolution SPR Sensor, Zhenchao Liu et al. (Year: 2020).*

* cited by examiner

*Primary Examiner* — Jacques M Saint Surin
(74) *Attorney, Agent, or Firm* — Mintz Levin Cohn Ferris Glovsky and Popeo, P.C.

(57) ABSTRACT

A method includes receiving data characterizing a speed of an acoustic signal through a gas mixture in a pipe. The speed of the acoustic signal can be detected by an ultrasonic flow meter coupled to the pipe. The method also includes receiving data characterizing a concentration of one or more inert gases in the gas mixture detected by an inert gas analyzer. The method further includes determining, based on the received data characterizing the speed of the acoustic signal and the received data characterizing the concentration of the one or more inert gases in the gas mixture, a net heating value of the gas mixture. The method also includes adjusting a processing of the gas mixture based on the determined net heating value.

20 Claims, 4 Drawing Sheets

ONLINE ANALYZERS FOR FLARE GAS PROCESSING

BACKGROUND

Ultrasonic measurement systems can be used to determine properties of a fluid flowing through a conduit (e.g., pipe). These systems can operate by creating an acoustic signal pulse, and transmitting the pulse through a fluid in a conduit, and receiving the signal after it has traveled along a path in the fluid. Important properties of the fluid can be determined as a function of the transit times of the acoustic signals.

It can be desirable to detect properties of surplus or waste fluids generated or released in an industrial process. For example, it can be desirable to determine the energy content of a flare or vent gas that can be indicative of the combustion efficiency of the flaring process. For example, the U.S. Environmental Protection Agency (EPA) regulations can stipulate that the combustion efficiency (or net heating value) of industrial flares is periodically measured and shown to have a value in a desirable range. Combustion efficiency of the flaring process can be determined, for example, based on composition of the flare/vent gas that can be measured by an online gas analyzer (e.g., gas chromatograph). Alternately or additionally, combustion efficiency of the flaring process can be calculated from the speed of sound (e.g., an acoustic signal) in the flare gas.

SUMMARY

In one implementation, a method includes receiving data characterizing a speed of an acoustic signal through a vent gas mixture in a pipe. The speed of the acoustic signal can be detected by an ultrasonic flow meter coupled to the pipe. The method also includes receiving data characterizing a concentration of one or more inert (non-combustible) gases in the vent gas mixture detected by an inert gas analyzer. The method further includes determining, based on the received data characterizing the speed of the acoustic signal and the received data characterizing the concentration of the one or more inert gases in the gas mixture, a net heating value of the gas mixture. The method also includes adjusting a processing of the gas mixture based on the determined net heating value.

One or more of the following features can be included in any feasible combination.

In one implementation, adjusting of the processing of the vent gas mixture includes receiving data characterizing a target net heating value and determining, based on the net heating value and the target net heating value, a flow rate of an assist gas configured to be added to the vent gas mixture. The adjusting of the processing of the vent gas mixture further includes adjusting the flow rate of the assist gas by at least controlling a first valve configured to control the flow of the assist gas to the gas mixture.

In one implementation, adjusting the processing of the vent gas mixture further includes determining a flow rate of a fuel gas configured to be added to the gas mixture. The determining is based on the net heating value, the target net heating value and flow rate of the assist gas. The adjusting of the processing of the gas mixture further includes adjusting the flow rate of the fuel gas by at least controlling a second valve configured to control the flow of the fuel gas to the mixture of gases.

In one implementation, adjusting the flow rate of the assist gas includes transmitting a control signal to an electronic controller associated with the first valve. In another implementation, determining the net heating value includes determining the total molecular weight of the gas mixture; determining, from the data characterizing the concentration of one or more inert gases, the molecular weight of hydrocarbons in the gas mixture; and determining, from the total molecular weight of the vent gas mixture and the molecular weight of hydrocarbons in the gas mixture, the net heating value. The net heating value is indicative of energy content of the combustible hydrocarbons in the gas mixture.

In one implementation, the inert gas analyzer includes an optical source configured to generate a radiation configured to interact with the vent gas mixture; and a first detection system configured to detect a first scattered light including a first wavelength and generated by an interaction of the radiation with a first gas in the gas mixture. An intensity of the first scattered light is indicative of a concentration of the first gas in the gas mixture. In another implementation, the first detection system includes a first detector, and a band pass filter configured to transmit light having the first wavelength.

In one implementation, the inert gas analyzer includes a second detection system configured to detect a second scattered light having a second wavelength and generated by an interaction of the radiation with a second gas in the gas mixture. An intensity of the second scattered light is indicative of a concentration of the second gas in the gas mixture. In another implementation, the inert gas analyzer is coupled to the pipe or coupled to a chamber configured to receive a portion of the vent gas mixture from the pipe.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions and information (e.g., look-up tables) that can cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

These and other capabilities of the disclosed subject matter will be more fully understood after a review of the following figures, detailed description, and claims.

BRIEF DESCRIPTION OF THE FIGURES

These and other features will be more readily understood from the following detailed description taken in conjunction with the accompanying drawings, in which.

DETAILED DESCRIPTION

Industrial processes (e.g., oil production) can generate one or more fluids (e.g., flare gas) as a surplus or by-product. Generation and release of flare gas (or vent gas) to the atmosphere may need to be regulated to ensure that the composition of the flare emission complies with industry standards (e.g., EPA regulations). The flare gas can be processed (e.g. to destroy hydrocarbons and/or volatile organic compounds in the vent gas via combustion) in order to make flare emissions compliant with environmental regulations based on industry standards (e.g., Clean Air Act). This can be accomplished by determining a net heating value of the flare gas and regulating the combustion of the flare gas based on this determination to ensure that the net heating value is in a predetermined range.

The net heating value can be calculated from the chemical composition of the flare gas (e.g., net heating value of each combustible component, concentration of various molecular species in the flare gas, etc.). The existing techniques of measuring the composition of the flare gas (e.g., gas chromatography) can take a long time and may need to be performed ex situ (e.g., in a lab away from the industrial plant processing flare gas). This can lead to a loss of productivity (e.g., by making the industrial combustion process less efficient, by requiring down time, etc.), may not replicate the actual operating conditions of the flare and can limit the accuracy of the measurement. Accordingly, methods and systems of flare gas processing based on in situ measurement (e.g., in the industrial plant processing flare gas) of flare gas composition and net heating value using an inert gas analyzer are provided. In situ detection of the composition of flare gas can allow for accurate and fast estimation of the net heating value of the flare gas, which in turn can allow for efficient processing (e.g., combustion, destruction, etc.) of the flare gas (e.g., in real-time).

Figure 1:
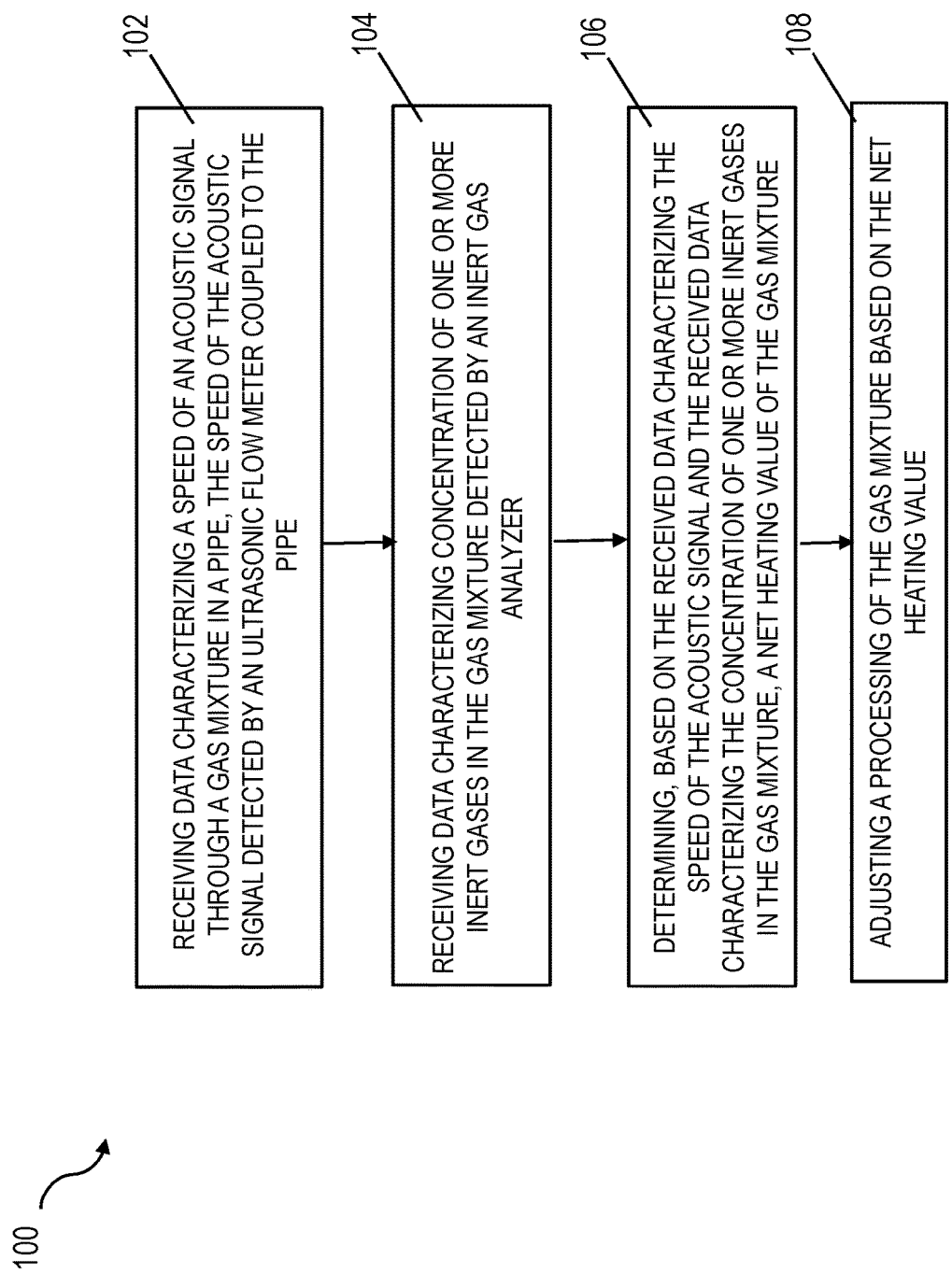
FIG. 1 is a flow chart of an exemplary method for in situ measurement of a net heating value of a flare gas.
Figure 2:
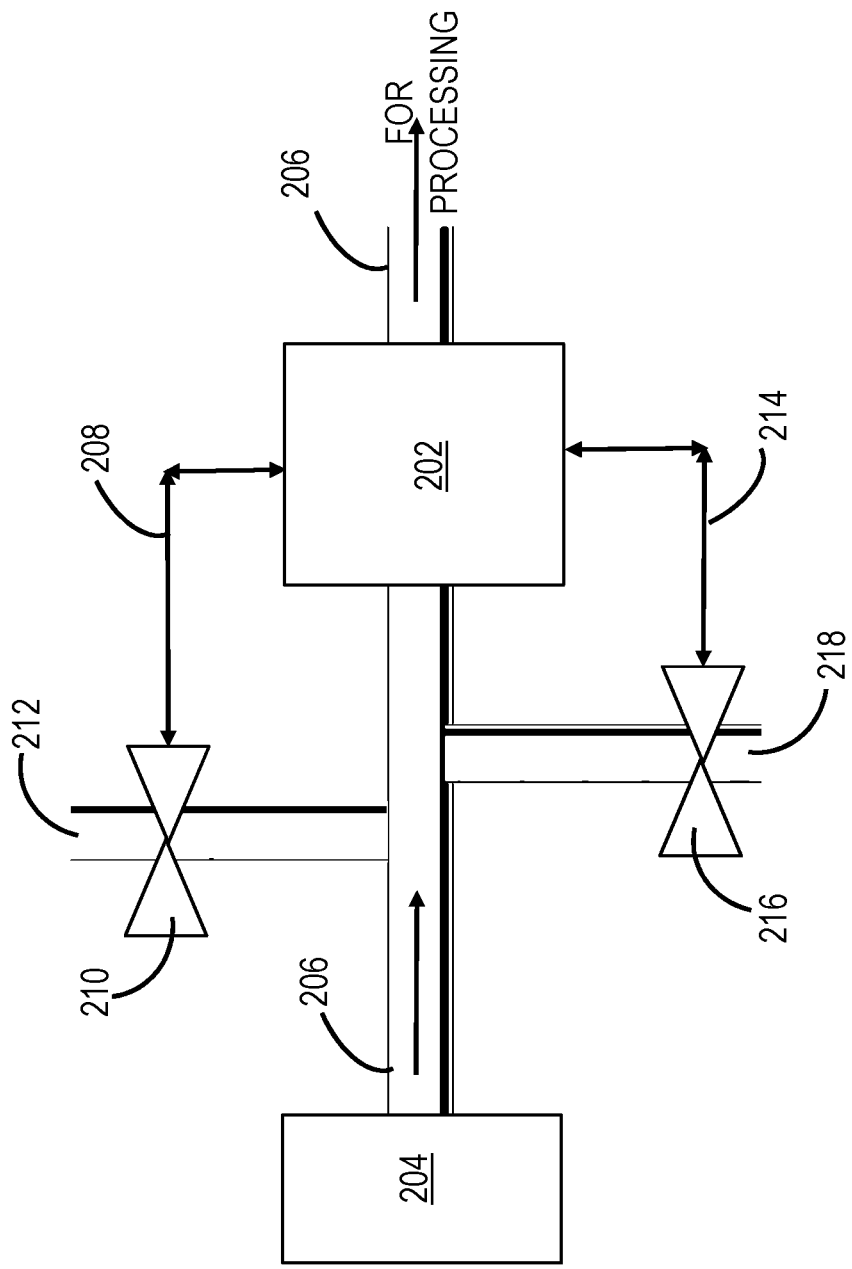
FIG. 2 is a schematic illustration of an exemplary industrial plant including an in situ net heating value (NHV) detection system.

FIG. 1 is a flow chart of an exemplary method for in situ measurement of the Net heating value of a flare gas by a net heating value (NHV) detection system in an industrial plant (e.g., an online NHV detection system). The net heating value (also known as lower heating value) of the flare gas can be indicative of the amount of heat released (e.g., in BTU) by combusting the hydrocarbon content in a specified quantity (e.g., a standard cubic foot or SCF) of the flare gas (e.g., after subtracting the latent heat of vaporization of water generated during combustion). At 102, data characterizing a speed of an acoustic signal through a gas mixture (e.g., flare gas) in a pipe can be received (e.g., by a computing device in the NHV detection system). The speed of the acoustic signal can be measured by an ultrasonic flow meter (e.g., included in the NHV system) coupled to the pipe that can transport a flare gas in an industrial system. In some implementations, the pipe transporting the flare gas can be a component of the NHV detection system. FIG. 2 is a schematic illustration of an exemplary industrial plant 200 including an in situ NHV detection system 202. The NHV detection system can receive gas mixture (e.g., flare/vent gas) from an industrial process 204 via pipe 206 (e.g., NHV detection system can be coupled to a pipe carrying the flare gas in the industrial plant). The NHV detection system 202 can detect the net heating value of the gas mixture and can control the processing of the vent gas mixture (e.g., based on industrial standards for processing flare gases). For example, the NHV detection system 202 can control the addition of an assist gas and/or a fuel gas to the vent gas mixture prior to the processing of the gas mixture (e.g., via combustion). Adding the assist and/or fuel gas can change the heating value of the flare gas and can allow for efficient processing (e.g., combustion) of the flare gas.

Figure 3:
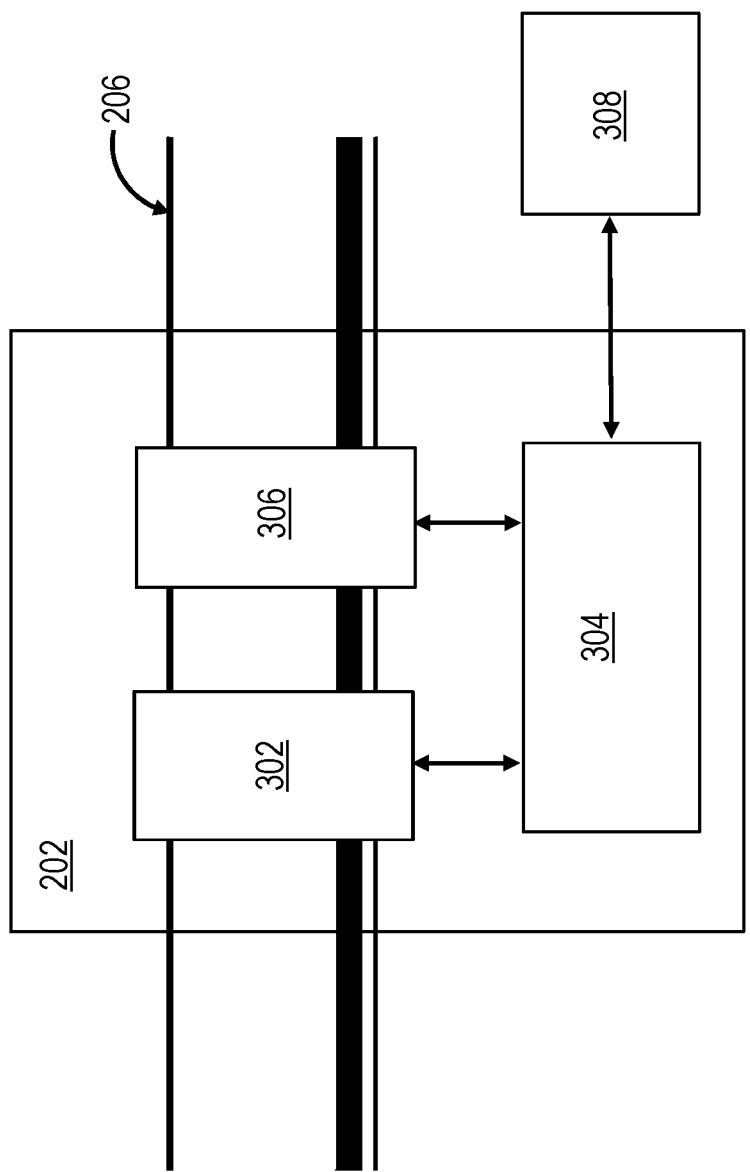
FIG. 3 is a schematic illustration of an exemplary NHV detection system in FIG. 2.

FIG. 3 is a schematic illustration of an exemplary NHV detection system 202 that can include a flow meter 302 configured to detect the speed of an acoustic signal through a gas mixture flowing through the pipe 206, an inert gas analyzer 306 that can detect concentration of various non-combustible gases in the gas mixture flowing through the pipe 206, and a computing device 304. The computing device 304 can be communicatively coupled to a user computing device 308. The flow meter 302 can be coupled to the pipe 206. In some implementations, the flow meter 302 can include a pair of ultrasonic transducers that can be separated by a path length that can extend across the pipe (e.g., across the diameter of the pipe). The transducers can be configured to transmit and/or receive an acoustic signal (e.g., an acoustic pulse). The flow meter 302 can include a detection system that can measure the time taken for an acoustic signal to travel along the fixed path length. Based on the time of travel and the path length between the transducers, the first speed of the acoustic signal can be determined. The path length can be predetermined (e.g., can be set to a predetermined value when the flow meter is installed on the pipe 206).

Figure 4:
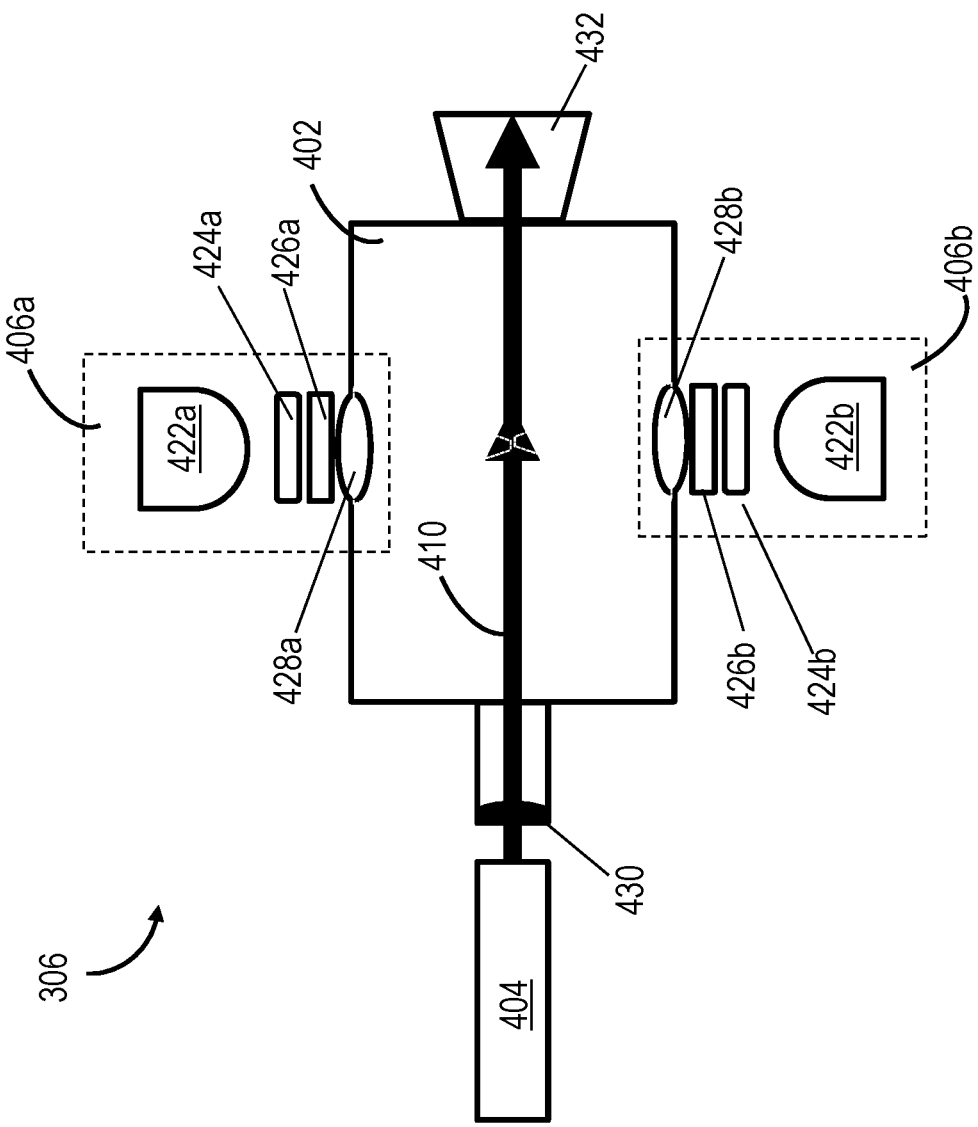
FIG. 4 illustrates an exemplary inert gas analyzer in the NHV detection system in FIG. 3.

Returning to FIG. 1, at 104, the computing device 304 can receive data characterizing the concentration of one or more inert gases in the gas mixture detected by an inert gas analyzer 306. In some implementations, the inert gas analyzer 306 can include a spectrometer that can detect the concentration of one or more inert gases in the gas mixture using laser spectroscopy. FIG. 4 illustrates an exemplary inert gas analyzer 306. The inert gas analyzer 306 can be coupled to a gas cell 402 that can enclose (e.g., by receiving) at least a portion of the gas mixture in the pipe 206. For example, the gas cell 402 can include a portion of the pipe 206 or can be a separate chamber configured to receive a portion of the gas mixture from the pipe 206.

The inert gas analyzer 306 can include a source 404 (e.g., a laser source, UV lamp, etc.) and detection systems 406a and 406b. The number of detection systems in the inert gas analyzer 306 is exemplary, and the inert gas analyzer 306 can include one or more detection systems. The source 404 can generate radiation 410 (e.g., a laser beam) at a known pre-determined wavelength that can interact with the gas mixture in the gas cell 402. The radiation 410 can be focused into the gas cell 402 by a lens 430. The gas mixture can scatter portions of the radiation 410 which can be detected by the detection systems 406a and 406b. Different gases in the gas mixture (e.g., inert gases) can interact differently with the radiation. For example, a first gas in the gas mixture can interact with the radiation 410 and generate a first scattered light. The first scattered light can include a first wavelength (e.g., in a first bandwidth), which can be indicative of the identity of the first gas. Similarly, a second gas in the gas mixture can interact with the radiation 410 and generate a second scattered light having a second wavelength (e.g., in a second bandwidth), which can be indicative of the identity of the second gas.

The detection system 406a can include a detector 422a, a band pass filter 424a, a notch filter 426a and a lens 428a. Similarly, the detection system 406b can include a detector 422b, a band pass filter 424b, a notch filter 426b and a lens 428b. The lens 428a can focus the scattered light generated in the gas cell 402 on the detector 422a. The band pass filter 424a and the notch filter 426a can attenuate scattered light outside the first bandwidth centered on the first wavelength. They can allow the detector 422a to primarily detect the first scattered light. The intensity of the first scattered light can be indicative of the concentration of the first gas (e.g., $N_2$, $O_2$, $H_2S$, etc.) in the gas mixture. Similarly, lens 428b can focus the scattered light generated in the gas cell 402 on the detector 422b. The band pass filter 424b and the notch filter 426b can attenuate scattered light outside the second bandwidth centered on the second wavelength. They can allow the detector 422b to primarily detect the second scattered light. The intensity of the second scattered light can be indicative of the concentration of the second inert gas (e.g., $N_2$, $O_2$, $H_2S$, etc.) in the gas mixture. For example, from a gas sample excited by a laser centered at 532 nm, the scattering spectrum of $O_2$ can be centered at about 560 nm and the scattering spectrum of $N_2$ can be centered at about 585 nm. A detection system (e.g., 406a, 406b, etc.) can be configured to detect $O_2$ (or $N_2$) by including a notch filter and a band pass filter having a transmission bandwidth that includes 560 nm (or 585 nm). Portions of the beam 410 that are not scattered by the gas mixture can be received and absorbed by the beam dump 432.

The optical detection systems 406a and 406b are faster than existing gas analyzers (e.g., gas chromatograph). This can allow for rapid detection/measurement/analysis of the composition and NHV of the vent gas mixture, which in turn can allow for fast and efficient adjustment of the processing of the gas mixture. Furthermore, detection systems 406a and 406b may not require removal of portions of gas mixture for ex situ analysis in laboratory conditions. This can improve the accuracy of the detection.

Returning to FIG. 1, at 106, the computing device 304 can determine the net heating value of the gas mixture based on the received data characterizing the speed of the acoustic signal and the received data characterizing the concentration of one or more components (e.g., inert gases) in the gas mixture. In some implementations, data characterizing the speed of the acoustic signal can include the path length traversed by the acoustic signal in the pipe 206, time of travel of the acoustic signal along the path length, and the like. The computing device 304 can calculate the speed of the acoustic signal (e.g., by dividing the path length by the time of travel of the acoustic length). The computing device 304 can determine the molecular weight of the gas mixture (e.g., average/total molecular weight of various gases in the gas mixture) based on a pre-determined algorithm that can include a molecular weight calculation based on the measured speed of sound (e.g., as described in U.S. Pat. No. 6,216,091). The molecular-weight-based algorithm can be based on a database of physical constants of a hydrocarbon mixture as a function of average molecular weight of the hydrocarbon mixture. The molecular-weight-based algorithm can be configured to iteratively set a hypothetical molecular weight and compute a predicted sound speed vs. the speed of acoustic signal detected by the flow meter 302. If the two speeds differ, a new molecular weight is set and the procedure is repeated until the predicted sound speed matches the measured sound speed, indicating that the current estimate is the correct average (or total) molecular weight.

As described above, data from the flow meter 302 can be used to calculate the average molecular weight of the gas mixture. However, in order to determine the net heating value of the gas mixture, it can be desirable to determine the molecular weight / concentration of hydrocarbons in the gas mixture (e.g., flare gas). This can be done, for example, by determining the concentration of gases that do not contribute to the net heating value. For example, inert gases (e.g., $N_2$, $O_2$, $H_2S$, etc.) can be present in the gas mixture and may not contribute to the net heating value. These inert gases may have been added to the gas mixture (e.g., during the industrial process 204, to generate a positive pressure, flush the pipelines of undesirable gases, etc.).

The received data characterizing the concentration of one or more gases in the gas mixture (e.g., from the inert gas analyzer 306) can include data indicative of an intensity of radiation detected by the detector (e.g., detector 422a, 422b, etc.). The computing device 304 can also receive data indicative of characteristics of the detection system (e.g., the gas that the detection system is configured to detect), pressure and temperature in the gas cell 402 (e.g., from pressure and temperature sensors in the gas cell 402), intensity of the radiation 410 (e.g., from the laser 404), etc. Based on one or more of the aforementioned pieces of information, the computing system 306 can measure the concentration of the inert gas that the detection system is configured to detect (e.g., based on choice of the notch and band pass filters in the detection system). From the concentration of the various inert gases in the pipe 206, the computing device can determine the molecular weight of the inert gases (e.g., average or total molecular weight by using a predetermined algorithm).

The computing device 304 can calculate the net heating value of the gas mixture (or flare gas) from the average (or total) molecular weight (e.g., determined based on data from flow meter 302) and molecular weight of the inert gases (e.g., determined based on data from inert gas analyzer 306). For example, the computing device 304 can calculate the molecular weight of hydrocarbons in the gas mixture from the average (or total) molecular weight and the concentration and molecular weight of the inert gases. In some implementations, by using the linear relationship between the molecular weight and net heating value of a gas mixture, a net heat value (NHV) calculation algorithm can calculate the net heating value based on the measured molecular weight of the hydrocarbons.

Returning to FIG. 1, at 108, processing of the gas mixture can be adjusted based on the net heating value calculated in step 106. In some implementations, the gas mixture (or flare gas) needs to be processed (e.g., combusted) prior to release of the gas mixture (e.g., to the environment). In some implementations, prior to the combustion of the gas mixture, its net heating value may need to be varied (e.g., set to a target net heating value). This can be done, for example, by adding an assist gas (e.g., steam or air) to the gas mixture. The assist gas can provide better mixing of the flare gas fuel with the oxidizing air, allow for smokeless combustion of the gas mixture, and protection of the flare tip associated with the combustion. Additionally or alternately, a fuel gas may be added to the gas mixture to increase the net heating value of the gas mixture. The fuel gas can also be used to maintain a certain NHV in the combustion zone to prevent extinguishing the flame or incomplete combustion of the flare gas.

The computing device 304 can receive data characterizing a target net heating value for the gas mixture. For example, a user can provide the target net heating value via the user computing device 308. Based on the target net heating value of the gas mixture and the calculated net heating value, the computing device 304 can calculate the mass/volumetric flow of assist gas that may need to be added to the gas mixture. The computing device may have access to assist gas characteristics (e.g., temperature, pressure, etc.) in the pipe 212. For example, the computing device can receive pressure/temperature of the assist gas in the pipe 212 from pressure/temperature sensors coupled to the pipe 212. Additionally or alternately, this information can be provided by the user via the user computing device 308. Based on the received pressure/temperature data and the calculated weight / volume of the assist gas to be added, the computing device 304 can determine the target flow rate of assist gas (e.g., by controlling the valve 210).

The computing device 304 can calculate the weight / volume of fuel gas that needs to be added to the gas mixture. The computing device 304 may have access to fuel gas characteristics (e.g., temperature, pressure, net heating value, etc.) in the pipe 218. For example, the computing device can receive characteristic data of the fuel gas in the pipe 218 from pressure/temperature sensors coupled to the pipe 218. Additionally or alternately, this information can be provided by the user via the user computing device 308. Based on one or more of the flow rate of the assist gas, the received characteristics of the fuel gas and the calculated weight / volume of the fuel gas to be added, the computing device 304 can determine the target flow rate of fuel gas (e.g., by controlling the valve 216).

In some implementations, the flow rate of the assist gas and fuel gas can be iteratively calculated. For example, after adjusting the flow rate of the assist and/or fuel gas, the net heating value of the gas mixture can be recalculated (e.g., as described in FIG. 1). Based on the recalculated net heating value, the flow rate of the assist gas and the fuel gas can be readjusted. This process can be repeated until the difference between the target net heating value and the calculated net heating value of the gas mixture is below a predetermined threshold value.

As illustrated in FIG. 2, the computing device 304 (in the NHV detection system 202) can transmit a first control signal 208 to the valve 210 that can control the flow of assist gas in the pipe 212. The pipe 212 is coupled to the pipe 206, and the assist gas can be transported to pipe 206 and added to the gas mixture in pipe 206. In some implementations, valve 210 can include an electronic (e.g., solenoid, piezoelectric, etc.) controller that can change the flow of assist gas based on the first control signal 208. For example, the flow of assist gas can be set to the target flow rate of the assist gas. The computing device 304 can transmit a second control signal 214 to the valve 216 that can control the flow of fuel gas in the pipe 218. The pipe 218 is coupled to the pipe 206, and the fuel gas can be transported to pipe 206 and added to the gas mixture in pipe 206. In some implementations, valve 216 can include a second electronic (e.g., solenoid, piezoelectric, etc.) controller that can change the flow of fuel gas based on the second control signal. For example, the flow of fuel gas can be set to the target flow rate of the fuel gas.

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus, within a particular embodiment, each feature of each like-named component is not necessarily fully elaborated upon.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules, and/or by one or more other devices, instead of or in addition to, the function performed at the particular module. Further, the modules can be implemented across multiple devices, and/or other components, local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web interface through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

What is claimed is:

1. A method comprising:
   receiving data characterizing a speed of an acoustic signal through a gas mixture in a pipe, the speed of the acoustic signal detected by an ultrasonic flow meter coupled to the pipe;
   receiving data characterizing a concentration of one or more inert gases in the gas mixture detected by an inert gas analyzer;
   determining, based on the received data characterizing the speed of the acoustic signal and the received data characterizing the concentration of the one or more inert gases in the gas mixture, a net heating value of the gas mixture; and
   adjusting a processing of the gas mixture based on the determined net heating value.

2. The method of claim 1, wherein the adjusting of the processing of the gas mixture comprising
   receiving data characterizing a target net heating value;
   determining, based on the net heating value and the target net heating value, a flow rate of an assist gas configured to be added to the gas mixture; and
   adjusting the flow rate of the assist gas by at least controlling a first valve configured to control the flow of the assist gas to the gas mixture.

3. The method of claim 2, wherein adjusting the processing of the gas mixture further comprising:
   determining a flow rate of a fuel gas configured to be added to the gas mixture, the determining based on the net heating value, the target net heating value and flow rate of the assist gas; and
   adjusting the flow rate of the fuel gas by at least controlling a second valve configured to control the flow of the fuel gas to the mixture of gases.

4. The method of claim 2, wherein adjusting the flow rate of the assist gas includes transmitting a control signal to an electronic controller associated with the first valve.

5. The method of claim 1, wherein determining the net heating value includes:
   determining, the total molecular weight of the gas mixture;
   determining, from the data characterizing the concentration of one or more inert gases, the molecular weight of hydrocarbons in the gas mixture; and
   determining, from the total molecular weight of the gas mixture and the molecular weight of hydrocarbons in the gas mixture, the net heating value.

6. The method of claim 5, wherein the net heating value is indicative of energy content of the hydrocarbons in the gas mixture.

7. The method of claim 1, wherein the inert gas analyzer includes:
   a source configured to generate a radiation configured to interact with the gas mixture; and
   a first detection system configured to detect a first scattered light including a first wavelength and generated by an interaction of the radiation with a first gas in the gas mixture, wherein an intensity of the first scattered light is indicative of a concentration of the first gas in the gas mixture.

8. The method of claim 7, wherein the first detection system includes:
   a first detector; and
   a band pass filter configured to transmit light having the first wavelength.

9. The method of claim 7, wherein the inert gas analyzer includes a second detection system configured to detect a second scattered light having a second wavelength and generated by an interaction of the radiation with a second gas in the gas mixture, wherein an intensity of the second scattered light is indicative of a concentration of the second gas in the gas mixture.

10. The method of claim 1, wherein the inert gas analyzer is coupled to the pipe or coupled to a chamber configured to receive a portion of the gas mixture from the pipe.

11. A system comprising:
   at least one data processor;
   memory coupled to the at least one data processor, the memory storing instructions to cause the at least one data processor to perform operations comprising:
      receiving data characterizing a speed of an acoustic signal through a gas mixture in a pipe, the speed of the acoustic signal detected by an ultrasonic flow meter coupled to the pipe;
      receiving data characterizing a concentration of one or more inert gases in the gas mixture detected by an inert gas analyzer;
      determining, based on the received data characterizing the speed of the acoustic signal and the received data characterizing the concentration of the one or more inert gases in the gas mixture, a net heating value of the gas mixture; and
      adjusting a processing of the gas mixture based on the determined net heating value.

12. The system of claim 11, wherein the adjusting of the processing of the gas mixture comprising
   receiving data characterizing a target net heating value;
   determining, based on the net heating value and the target net heating value, a flow rate of an assist gas configured to be added to the gas mixture; and
   adjusting the flow rate of the assist gas by at least controlling a first valve configured to control the flow of the assist gas to the gas mixture.

13. The system of claim 12, wherein adjusting the processing of the gas mixture further comprising:
   determining a flow rate of a fuel gas configured to be added to the gas mixture, the determining based on the net heating value, the target net heating value and flow rate of the assist gas; and
   adjusting the flow rate of the fuel gas by at least controlling a second valve configured to control the flow of the fuel gas to the mixture of gases.

14. The system of claim 12, wherein adjusting the flow rate of the assist gas includes transmitting a control signal to an electronic controller associated with the first valve.

15. The system of claim 11, wherein determining the net heating value includes:
   determining, the total molecular weight of the gas mixture;
   determining, from the data characterizing the concentration of one or more inert gases, the molecular weight of hydrocarbons in the gas mixture; and
   determining, from the total molecular weight of the gas mixture and the molecular weight of hydrocarbons in the gas mixture, the net heating value.

16. The system of claim 15, wherein the net heating value is indicative of energy content of the hydrocarbons in the gas mixture.

17. The system of claim 11, wherein the inert gas analyzer includes:
   a source configured to generate a radiation configured to interact with the gas mixture; and
   a first detection system configured to detect a first scattered light including a first wavelength and generated by an interaction of the radiation with a first gas in the gas mixture, wherein an intensity of the first scattered light is indicative of a concentration of the first gas in the gas mixture.

18. The system of claim 17, wherein the first detection system includes:
   a first detector; and
   a band pass filter configured to transmit light having the first wavelength.

19. The system of claim 17, wherein the inert gas analyzer includes a second detection system configured to detect a second scattered light having a second wavelength and generated by an interaction of the radiation with a second gas in the gas mixture, wherein an intensity of the second scattered light is indicative of a concentration of the second gas in the gas mixture.

20. The system of claim 11, wherein the inert gas analyzer is coupled to the pipe or coupled to a chamber configured to receive a portion of the gas mixture from the pipe.

* * * * *